United States Patent [19]

Holmwood et al.

[11] Patent Number: 4,499,281

[45] Date of Patent: Feb. 12, 1985

[54] SUBSTITUTED TRIAZOLYLMETHYL-OXIRANES AND THEIR USE AS INTERMEDIATES FOR FUNGICIDES

[75] Inventors: Graham Holmwood; Erik Regel, both of Wuppertal, Fed. Rep. of Germany

[73] Assignee: Bayer Aktiengesellschaft, Leverkusen, Fed. Rep. of Germany

[21] Appl. No.: 352,689

[22] Filed: Feb. 26, 1982

[30] Foreign Application Priority Data

Mar. 21, 1981 [DE] Fed. Rep. of Germany ....... 3111238

[51] Int. Cl.³ .................. A01N 43/64; C07D 249/08; C07D 405/06
[52] U.S. Cl. ........................................ 548/262; 71/76; 71/92
[58] Field of Search ......................... 548/262; 424/269

[56] References Cited

U.S. PATENT DOCUMENTS 3,156,554 11/1964 Tolbert ................................. 71/2.7
4,301,166 11/1981 Regel et al. ......................... 568/808

FOREIGN PATENT DOCUMENTS 0023103 1/1981 European Pat. Off. ............ 548/336
0026312 4/1981 European Pat. Off. .
0044605 1/1982 European Pat. Off. .
0044422 1/1982 European Pat. Off. .
0061835 10/1982 European Pat. Off. ............ 548/262
1667968 3/1972 Fed. Rep. of Germany .
2908378 9/1980 Fed. Rep. of Germany ...... 548/262

OTHER PUBLICATIONS

Heterocycles, vol. 8, p. 397 (1977).

Primary Examiner—Alton D. Rollins
Attorney, Agent, or Firm—Sprung, Horn, Kramer & Woods

[57] ABSTRACT

A substituted triazolylmethyl-oxirane of the formula

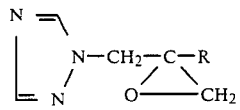

in which R is optionally substituted alkyl, aryl or cycloalkyl is prepared by reacting a triazolyl-ketone of the formula

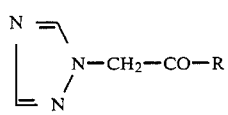

with (a) dimethyloxosulphonium methylide of the formula

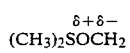

or (b) trimethylsulphonium methylsulphate of the formula

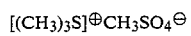

in the presence of a diluent.

The end product can then be reacted with a phenol of the formula

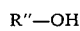

R″—OH to produce known fungicidally active compounds of the formula

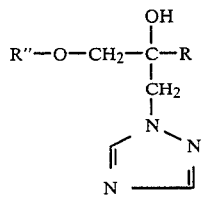

in which R″ is optionally substituted phenyl.

6 Claims, No Drawings

SUBSTITUTED TRIAZOLYLMETHYL-OXIRANES AND THEIR USE AS INTERMEDIATES FOR FUNGICIDES

The present invention relates to certain new substituted triazolylmethyl-oxiranes, to a process for their preparation, and to their use as intermediates for the preparation of plant protection agents.

It has already been disclosed that 2-chloroethyl-trimethyl-ammonium chloride and 2-chloroethylphosphoric acid exhibit plant growth-regulating properties (see U.S. Pat. No. 3,156,554 and German published specification No. 1,667,968). However, the activity of these compounds is not always adequate, especially if small amounts are used.

The present invention now provides, as novel compounds, the substituted triazolylmethyl-oxiranes of the general formula

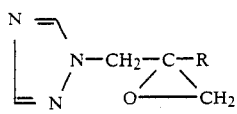  (I)

in which R represents optionally substituted alkyl, optionally substituted aryl or optionally substituted cycloalkyl.

The invention also provides a process for the preparation of a substituted triazolylmethyl-oxirane of the formula (I), in which a triazolyl-ketone of the general formula

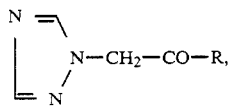  (II)

in which R has the abovementioned meaning, (a) is reacted with dimethyloxosulphonium methylide, of the formula

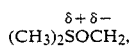  (III)

in the presence of a diluent, or (b) is reacted with trimethylsulphonium methylsulphate, of the formula

  (IV), in the presence of an inert organic solvent and in the presence of a base.

The substituted triazolylmethyl-oxiranes of the formula (I) can be used as intermediates for the synthesis of 1-hydroxyethyl-triazole derivatives which possess plant growth-regulating properties and fungicidal properties.

Surprisingly, the 1-hydroxyethyl-triazole derivatives, which can be prepared from the substituted triazolylmethyl-oxiranes according to the invention, are superior, in respect of their plant growth-regulating properties, to the previously known, very active compounds 2-chloroethyltrimethylammonium chloride and 2-chloroethylphosphonic acid. Accordingly, the compounds according to the invention, as intermediates for the synthesis of high-quality plant growth regulators and fungicides, represent a considerable enrichment of the art.

Formula (I) provides a general definition of the compounds according to the invention. Preferably, in this formula, R represents optionally substituted, straight-chain or branched alkyl with 1 to 4 carbon atoms, preferred substituents being halogen, alkoxy and alkylthio, each with 1 to 4 carbon atoms, halogenoalkoxy and halogenoalkylthio, each with 1 to 2 carbon atoms and 1 to 5 identical or different halogen atoms (such as fluorine and chlorine atoms), cyano, alkoxycarbonyl with 1 to 4 carbon atoms in the alkoxy part, and optionally substituted phenyl, phenoxy and benzyloxy, suitable substituents on the phenyl being, in each case, halogen, alkyl with 1 to 4 carbon atoms and halogenoalkyl, halogenoalkoxy and halogenoalkylthio, each with 1 to 2 carbon atoms and 1 to 5 identical or different halogen atoms (such as fluorine and chlorine atoms); or represents optionally substituted phenyl, preferred substituents being halogen, alkyl with 1 to 4 carbon atoms and halogenoalkyl, halogenoalkoxy and halogenoalkylthio, each with 1 to 2 carbon atoms and 1 to 5 identical or different halogen atoms (such as fluorine and chlorine atoms); or represents cycloalkyl with 3 to 7 carbon atoms, optionally substituted by alkyl with 1 to 4 carbon atoms.

Particularly preferred compounds of the formula (I) are those in which

R represents optionally substituted alkyl of the general formula

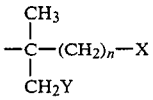

wherein

X represents hydrogen, halogen (especially fluorine or chlorine), alkoxy or alkylthio, in either case with 1 to 4 carbon atoms, halogenoalkoxy or halogenoalkylthio, in either case with 1 to 2 carbon atoms and 1 to 5 identical or different halogen atoms (especially fluorine and chlorine atoms), cyano, alkoxycarbonyl with 1 to 4 carbon atoms in the alkoxy part, or optionally substituted phenyl, phenoxy or benzyloxy, the preferred substituents on the phenyl in each case being chlorine, fluorine, methyl and ethyl, Y represents hydrogen or halogen (especially fluorine or chlorine), and n represents 0 or 1.

Further particularly preferred compounds of the formula (I) are those in which R represents optionally substituted phenyl, the substituents being halogen (especially fluorine and chlorine), alkyl with 1 to 4 C atoms and halogenoalkyl, halogenoalkoxy and halogenoalkylthio, each with 1 to 2 C atoms and 1 to 5 identical or different halogen atoms (especially fluorine and chlorine atoms).

Further particularly preferred compounds of the formula (I) are those in which R represents cycloalkyl with 3 to 6 carbon atoms, optionally substituted by alkyl with 1 to 2 carbon atoms.

The following exemplary compounds of the general formula (I) may be mentioned, in addition to the compounds mentioned later in the preparative examples:

TABLE 1

$$\begin{array}{c} N = \\ \Big| \quad \diagdown \\ \quad \quad N - CH_2 - C - R \\ / \quad \quad \diagup \diagdown \\ = N \quad \quad O \longrightarrow CH_2 \end{array} \quad (I)$$

| R | R |
|---|---|
| —C(CH₃)₂—CH₂Cl | —C(CH₃)₂—CH₂F |
| —C(CH₂Cl)₂—CH₃ | —C(CH₂F)₂—CH₃ |
| —C(CH₃)₂—COOCH₃ | —C(CH₃)₂—COOC₂H₅ |
| —C(CH₃)₂—⟨C₆H₄⟩—Cl | —C(CH₃)₂—O—⟨C₆H₄⟩—Cl |
| —C(CH₃)₂—CH₂—⟨C₆H₄⟩—Cl | —C(CH₃)₂—CH₂—O—⟨C₆H₄⟩—Cl |
| —C(CH₃)₂—CH₂—O—CH₃ | —C(CH₃)₂—CH₂—O—C₂H₅ |
| —C(CH₃)₂—SCF₃ | —C(CH₃)₂—CH₂—CN |
| —CH(CH₃)₂ | |
| | —⟨C₆H₄⟩—Cl |
| —⟨C₆H₁₁⟩H (cyclohexyl) | —C(CH₃)(cyclopropyl) |

If, for example, 3,3-dimethyl-1-(1,2,4-triazol-1-yl)-butan-2-one and trimethyloxosulphonium iodide and sodium hydride (in situ preparation of dimethyloxosulphonium methylide) are used as starting materials in process variant (a), the course of the reaction can be represented by the following equation:

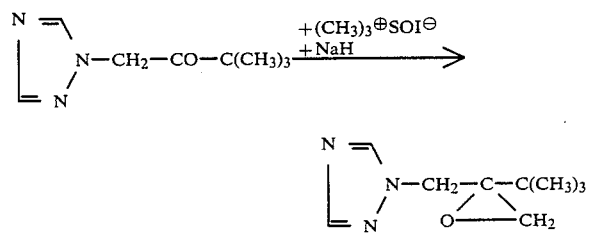

If, for example, 3,3-dimethyl-1-(1,2,4-triazol-1-yl)-butan-2-one, dimethyl sulphide and dimethyl sulphate (in situ preparation of trimethylsulphonium methylsulphate) are used as starting materials and sodium methylate is used as the base in process variant (b), the course of the reaction can be represented by the following equation:

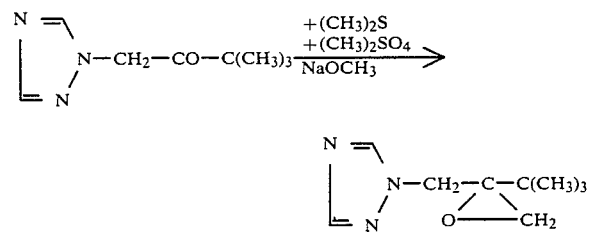

The formula (II) provides a general definition of the triazolyl-ketones to be used as starting materials for process variants (a) and (b). In this formula, R preferably represents those radicals which have already been mentioned above as preferred when describing the compounds of the formula (I).

Some of the triazolyl-ketones of the formula (II) are known (see, for example, German patent application Nos. 2,431,407, 2,610,022, 2,638,470 and 2,820,361), while some are the subject of an earlier application which has not yet been published. They are obtained by reacting halogenoketones of the general formula $$\text{Hal}-CH_2-CO-R \quad (V),$$

in which

R has the abovementioned meaning and
Hal represents chlorine or bromine, with 1,2,4-triazole in the presence of a diluent, for example acetone, and in the presence of an acid-binding agent, for example potassium carbonate, at temperatures of between 20° and 150° C.

The halogenoketones of the formula (V) are obtained by treating ketones of the general formula $$CH_3-CO-R \quad (VI),$$

in which R has the abovementioned meaning, with chlorine or bromine in an inert organic solvent at room temperature, or reacting them with, for example, any of the customary chlorinating agents, such as sulphuryl chloride, at from 20° to 60° C.

The dimethylsulphonium methylide of the formula (III), additionally, required as a starting material for process variant (a), is known (see J. Amer. Chem. Soc. 87, 1363–1364)). It is employed in the freshly prepared state by generating it in situ by reacting trimethyloxosulphonium iodide with sodium hydride or sodium amide in the presence of a diluent.

The trimethylsulphonium methylsulphate of the formula (IV), furthermore required as a starting material for process variant (b), is also known (see Heterocycles 8, 397 (1977)). It is also employed in a freshly prepared state, by producing it in situ by reacting dimethyl sulphide with dimethyl sulphate.

Preferred diluents for process variant (a) are dimethyl sulphoxide and mixtures of dimethyl sulphoxide with other inert organic solvents, for example tetrahydrofuran.

In carrying out process variant (a), the reaction temperatures can be varied within a substantial range. In general, the reaction is carried out at temperatures of between −10° C. and +80° C., preferably between 0° and 50° C.

Process variant (a) and the working up of the reaction mixture produced may be carried out in accordance with customary methods (see J. Amer. Chem. Soc. 87, 1363–1364 (1965)).

The preferred inert organic solvent for process variant (b) is acetonitrile.

Bases which can be used for process varient (b) are any of the customary strong inorganic or organic bases, preferably sodium methylate or potassium tert.-butylate.

In carrying out process variant (b), the reaction temperatures can be varied within a substantial range. In general, the reaction is carried out at temperatures of between 0° C. and 60° C., preferably at room temperature.

Process variant (b) and the working up of the reaction mixture produced may be carried out in accordance with customary methods (compare Heterocycles 8, 397 (1977)).

As already mentioned above, the substituted triazolylmethyl-oxiranes of the formula (I) are suitable as intermediate products for the synthesis of 1-hydroxyethyltriazole derivatives, which possess powerful plant growth-regulating properties and fungicidal properties.

Thus, for example, a 1-hydroxyethyltriazole derivative of the general formula

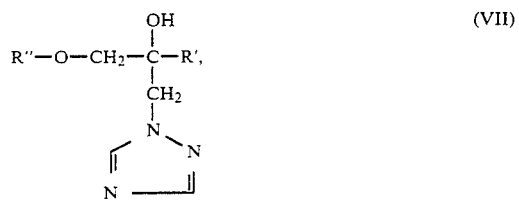

in which
R' represents alkyl, optionally substituted cycloalkyl or optionally substituted phenyl
and
R'' represents optionally substituted phenyl, can be prepared by reacting a substituted triazolylmethyloxirane of the general formula

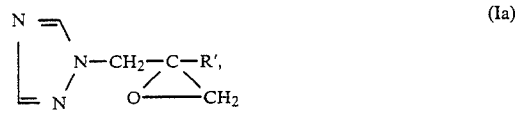

in which R' has the abovementioned meaning, with a phenol of the general formula

in which
R'' has the abovementioned meaning, in the presence of an inert organic solvent, for example ethanol, and, if appropriate, in the presence of a base, for example sodium methylate, if appropriate under a pressure of 1 to 25 bar, at a temperature between 60° C. and 150° C. This reaction, and the working up of the reaction mixture produced, may be carried out in accordance with customary methods (see the preparative examples).

In the compounds of the formula (Ia), R' preferably represents straight-chain or branched alkyl with 1 to 4 carbon atoms, substituted cycloalkyl with 3 to 7 carbon atoms, as well as phenyl which can have one or more substituents independently selected from halogen, alkyl with 1 to 4 carbon atoms and halogenoalkyl with 1 or 2 carbon atoms and 1 to 5 identical or different halogen atoms (such as fluorine atoms and chlorine atoms).

The formula (VIII) provides a general definition of the phenols required as reactants for the above reaction. In this formula, R'' preferably represents phenyl which can have one, two or three substituents selected independently from halogen, alkyl with 1 to 4 carbon atoms, cycloalkyl with 5 to 7 carbon atoms, alkoxy and alkylthio, each with 1 to 4 carbon atoms, halogenoalkyl, halogenoalkoxy and halogenoalkylthio, each with 1 to 2 carbon atoms and 1 to 5 identical or different halogen atoms (such as, in particular, fluorine atoms and chlorine atoms), or represents optionally substituted phenyl, optionally substituted phenoxy or optionally substituted phenylalkyl or phenylalkoxy with 1 to 2 carbon atoms in the alkyl part or in the alkoxy part, preferred substituents being halogen and alkyl with 1 to 4 carbon atoms.

The phenols of the formula (VIII) are generally known compounds of organic chemistry.

PREPARATIVE EXAMPLES

EXAMPLE 1

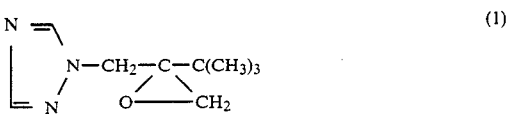

Process variant (a):

6.0 g of sodium hydride (80% strength in paraffin oil) and 44 g of trimethylsulphoxonium iodide were placed under a dry nitrogen atmosphere and 200 ml of absolute dimethyl sulphoxide were added slowly, at 10°–15° C. internal temperature. When the evolution of hydrogen had subsided, stirring was continued for 15 minutes and a solution of 30.1 g of 3,3-dimethyl-1-(1,2,4-triazol-1-yl)-butan-2-one in 50 ml of absolute tetrahydrofuran was then added dropwise while cooling to 20° C. internal temperature. Stirring is then continued for 1½ hours at 50° C.

The solvents were stripped off in a high vacuum, saturated sodium chloride solution was added to the residue and the mixture was extracted six times with ethyl acetate. The combined ethyl acetate phases were dried over sodium sulphate and concentrated, and the residue was distilled in a high vacuum. 23.5 g (72% of theory) of 2-tert.-butyl-2-(1,2,4-triazol-1-yl)-methyl-oxirane were obtained, having a boiling point of 68°–72° C./0.008 mbar and a refractive index of $n_D^{20} = 1.4809$.

EXAMPLE 2

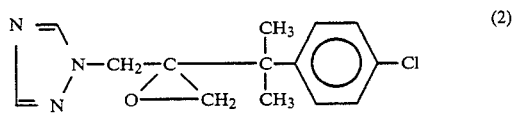

Process variant (a):

3.6 g (0.12 mol) of sodium hydride (80% strength in paraffin oil) and 26.5 g (0.12 mol) of trimethylsulphoxonium iodide were mixed under a nitrogen atmosphere, at 10° C., and 100 ml of dimethylsulphoxide were added slowly. After one hour, 26.35 g (0.1 mol) of 3-(4-chlorophenyl)-3-methyl-1-(1,2,4-triazol-1-yl)-butan-2-one, dissolved in 50 ml of dimethyl sulphoxide, were added dropwise to the suspension.

The mixture was stirred for 2 days at room temperature and was then heated for 5 hours to 60° C. and stirred into 3,000 ml of water. The oil which had separated out was taken up in chloroform and the solution was washed with water, dried over sodium sulphate and evaporated down in vacuo.

21 g (76% of theory) of 2-(4-chloro-α,α-dimethylbenzyl)-2-(1,2,4-triazol-1-yl)-methyl-oxirane were obtained having a refractive index $n_D^{20} = 1.5412$.

The following compounds of the general formula (I) were obtained according to the methods described in Examples 1 and 2.

TABLE 2

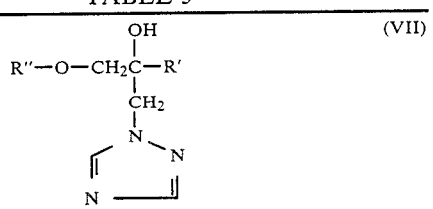

| Compound No. | R | Physical constants |
|---|---|---|
| 3 | —C(CH$_3$)$_2$CH$_2$F | $n_D^{20}$ = 1.4805 |
| 4 | —C(CH$_3$)$_2$CH$_2$OCH$_3$ | b.p.: 90–92° C./ 0.008 mbar |
| 5 | —C(CH$_3$)$_2$CH$_2$OC$_2$H$_5$ | b.p.: 83–85° C./ 0.007 mbar |
| 6. | 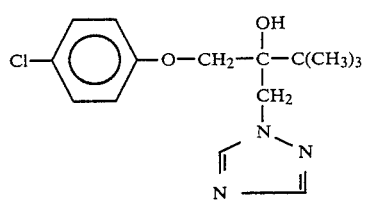 —C(CH$_3$)$_2$CH$_2$O—⟨ ⟩—Cl | m.p.: 70–71° C. |

PREPARATION OF THE END PRODUCTS

EXAMPLE 3

(VII-1)

Cl—⟨ ⟩—O—CH$_2$—C(OH)—C(CH$_3$)$_3$
               |
               CH$_2$
               |
               N—N
               ‖  ‖
               N—

9.9 g of 4-chlorophenol were added to a solution of 0.39 g of sodium in 130 ml of absolute ethanol. 10.8 g of tert.-butyl-2-(1,2,4-triazol-1-yl)-methyl-oxirane, dissolved in 34 ml of absolute ethanol, were then added, and the reaction mixture was heated under reflux overnight.

Thereafter the reaction mixture was concentrated, the residue was taken up in ethyl acetate and this mixture was washed once with water, once with 1N sodium hydroxide solution, then twice with water, and once with saturated sodium chloride solution.

The ethyl acetate phase was dried over sodium sulphate and concentrated. The residue was chromatographed over a silica gel column (mobile phase: methylene chloride/ethyl acetate=2:1). After recrystallization from ligroin, 13.0 g (70.5% of theory) of 2-(4-chlorophenoxy)-methyl-3,3-dimethyl-1-(1,2,4-triazol-1-yl)-butan-2-ol were obtained, having a melting point of 89°–91° C.

The compounds of the formula (VII) listed in terms of their formulae in the table which follows were obtained analogously.

TABLE 3

(VII)

R″—O—CH$_2$—C(OH)(R′)—CH$_2$—N(triazole)

| Compound No. | R″ | R′ | Melting point (°C.) |
|---|---|---|---|
| VII-2 | 4-Cl-phenyl, 2-CH$_3$ | —C(CH$_3$)$_3$ | 125.5–129 |
| VII-3 | 2,4-diCl-phenyl | —C(CH$_3$)$_3$ | 120.5–123.5 |
| VII-4 | 4-CH$_3$-phenyl | —C(CH$_3$)$_3$ | 98–101.5 |
| VII-5 | 2-CH$_3$-phenyl | —C(CH$_3$)$_3$ | 89–101 |

The good plant growth-regulating activity of 1-hydroxyethyltriazole derivatives of the formula (VII) can be seen from the examples which follow.

In these examples, the compounds listed below were employed as comparison substances:

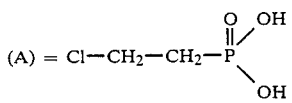

(A) = Cl—CH$_2$—CH$_2$—P(=O)(OH)(OH)

(2-chloroethyl-phosphonic acid)

(B) = Cl—CH$_2$—CH$_2$—N$^⊕$(CH$_3$)$_3$ Cl$^⊖$ (2-chloroethyltrimethylammonium chloride).

EXAMPLE 4

Inhibition of growth of sugar beet

Solvent: 30 parts by weight of dimethylformamide
Emulsifier: 1 part by weight of polyoxyethylene sorbitan monolaurate To produce a suitable preparation of active compound, 1 part by weight of active compound was mixed with the stated amounts of solvent and emulsifier and the mixture was made up to the desired concentration with water.

Sugar beet was grown in a greenhouse until formation of the cotyledons was complete. In this stage, the plants were sprayed with the preparations of active compound until dripping wet. After 14 days, the additional growth of the plants was measured and the inhibition of growth in percent of the additional growth of the control plants was calculated. 0% inhibition of growth denoted a growth which corresponded to that of the control plants. 100% inhibition of growth meant that growth had stopped.

In this test, active compounds VII-1 and VII-4 exhibited better inhibition of growth than the substance (B) known from the prior art.

EXAMPLE 5

Inhibition of growth of soy beans

Solvent: 10 parts by weight of methanol
Emulsifier: 2 parts by weight of polyoxyethylene sorbitan monolaurate To produce a suitable preparation of active compound, 1 part by weight of active compound was mixed with the stated amounts of solvent and emulsifier and the mixture was made up to the desired concentration with water.

Young soy bean plants, in the stage in which the first secondary leaves had unfolded, were sprayed with the preparations of active compound until dripping wet. After 2 weeks, the additional growth was measured and the inhibition of growth in % of the additional growth of the control plants was calculated. 100% meant that growth had stopped and 0% denoted a growth corresponding to that of the untreated control plants.

In this test, active compounds VII-1 and VII-2 exhibited better inhibition of growth than the substance (B) known from the prior art.

EXAMPLE 6

Inhibition of growth of cotton

Solvent: 30 parts by weight of dimethylformamide
Emulsifier: 1 part by weight of polyoxyethylene sorbitan monolaurate To produce a suitable preparation of active compound, 1 part by weight of active compound was mixed with the stated amounts of solvent and emulsifier and the mixture was made up to the desired concentration with water.

Cotton plants were grown in a greenhouse until the 5th secondary leaf had unfolded completely. In this stage, the plants were sprayed with the preparations of active compound until dripping wet. After 3 weeks, the additional growth of the plants was measured and the inhibition of growth in percent of the additional growth of the control plants was calculated. 100% inhibition of growth meant that growth had stopped and 0% denoted a growth corresponding to that of the control plants.

In this test, active compounds VII-1 and VII-4 exhibited better inhibition of growth than the substance (A) known from the prior art.

It will be understood that the specification and examples are illustrative but not limitative of the present invention and that other embodiments within the spirit and scope of the invention will suggest themselves to those skilled in the art.

We claim:

1. A substituted triazolylmethyl-oxirane of the formula

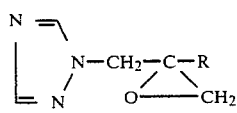

in which

R represents alkyl with 1 to 4 carbon atoms which optionally carries one or more substituents selected from halogen, alkoxy with 1 to 4 carbon atoms, alkylthio with 1 to 4 carbon atoms, halogenoalkoxy with 1 or 2 carbon atoms and 1 to 5 identical or different halogen atoms, halogenoalkylthio with 1 or 2 carbon atoms and 1 to 5 identical or different halogen atoms, cyano, alkoxycarbonyl with 1 to 4 carbon atoms in the alkoxy part, phenyl (which optionally carries one or more substituents selected from halogen, alkyl with 1 to 4 carbon atoms, halogenoalkyl with 1 or 2 carbon atoms and 1 to 5 identical or different halogen atoms, halogenoalkoxy with 1 or 2 carbon atoms and 1 to 5 identical or different halogen atoms and halogenoalkylthio with 1 or 2 carbon atoms and 1 to 5 identical or different halogen atoms), phenoxy (which optionally carries one or more substituents selected from halogen, alkyl with 1 to 4 carbon atoms, halogenoalkyl with 1 or 2 carbon atoms and 1 to 5 identical or different halogen atoms, halogenoalkoxy with 1 or 2 carbon atoms and 1 to 5 identical or different halogen atoms and halogenoalkylthio with 1 or 2 carbon atoms and 1 to 5 identical or different halogen atoms) and benzyloxy (which optionally carries one or more substituents on the phenyl part selected from halogen, alkyl with 1 to 4 carbon atoms, halogenoalkyl with 1 or 2 carbon atoms and 1 to 5 identical or different halogen atoms, halogenoalkoxy with 1 or 2 carbon atoms and 1 to 5 identical or different halogen atoms and halogenoalkylthio with 1 or 2 carbon atoms and 1 to 5 identical or different halogen atoms), or
R represents cycloalkyl with 3 to 7 carbon atoms which is optionally substituted by alkyl with 1 to 4 carbon atoms.

2. A substituted triazolylmethyl-oxirane according to claim 1, wherein such compound is 2-tert-butyl-2-(1,2,4-triazol-1-yl)-methyl-oxirane of the formula

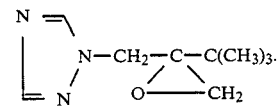

3. A substituted triazolylmethyl-oxirane according to claim 1, wherein such compound is 2-(4-chloro-α,α-dimethyl-benzyl)-2-(1,2,4-triazol-1-yl)-methyl-oxirane of the formula

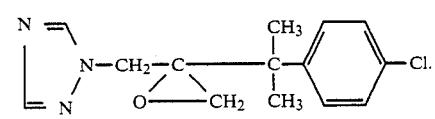

4. A compound according to claim 1, wherein such compound is 2-fluoro-tert.-butyl-2-(1,2,4-triazol-1-yl)-methyl-oxirane of the formula

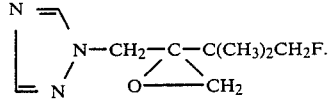
5. A compound according to claim 1, wherein such compound is 2-methoxy-tert.-butyl-2-(1,2,4-triazol-1-yl)-methyl-oxirane of the formula
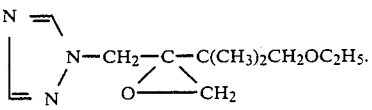
6. A compound according to claim 1, wherein such compound is 2-ethoxy-tert.-butyl-2-(1,2,4-triazol-1-yl)-methyl-oxirane of the formula
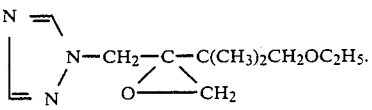
* * * * *